United States Patent [19]

Janoff et al.

[11] Patent Number: 4,564,599

[45] Date of Patent: Jan. 14, 1986

[54] LIPOSOME COMPOSITION FOR LUPUS ASSAY

[75] Inventors: Andrew S. Janoff, Lawrenceville; Marc J. Ostro, North Brunswick; Allan L. Weiner, Plainsboro, all of N.J.; Gerald Weissmann, New York, N.Y.; James R. Seibold, Piscataway, N.J.

[73] Assignee: The Lipodome Company, Inc., Princeton, N.J.

[21] Appl. No.: 476,495

[22] Filed: Mar. 24, 1983

Related U.S. Application Data

[63] Continuation-in-part of Ser. No. 410,249, Aug. 23, 1982, and a continuation-in-part of Ser. No. 362,382, Mar. 26, 1982.

[51] Int. Cl.[4] .................... G01N 33/564; B32B 5/16; B32B 9/02; B32B 9/04; A01N 25/00; A61K 9/42
[52] U.S. Cl. .................................. 436/507; 436/506; 436/829; 428/402.2; 424/7.1; 424/38
[58] Field of Search ................ 424/7.1, 38; 436/506, 436/507, 508, 513, 829; 428/402.2

[56] References Cited

U.S. PATENT DOCUMENTS

| 4,235,792 | 11/1980 | Hsia et al. | 436/829 |
| 4,329,331 | 5/1982 | Kallick | 436/506 |
| 4,448,765 | 5/1984 | Ash et al. | 436/829 |

FOREIGN PATENT DOCUMENTS

WO80/00026 1/1980 PCT Int'l Appl. ................ 436/506

OTHER PUBLICATIONS

Schieren, H. et al., Biochem. and Biophys. Res. Comm., 82 (4), pp. 1160–1167, (1978).
Weissmann, G. et al. I, J. Clin. Inves., 53, pp. 536–543, (Feb. 1974).
Weissmann, G. et al. II, Proc. Natl. Acad. Sci., U.S.A., 73 (2), pp. 510–514, (Feb. 1976).

*Primary Examiner*—Sidney Marantz
*Assistant Examiner*—L. Krawczewicz
*Attorney, Agent, or Firm*—Pennie & Edmonds

[57] ABSTRACT

An assay for detecting SLE antibodies utilizing a novel liposome composition in which there is entrapped a divalent cation responsive indicator. The presence of such antibodies is detected by their stabilization of the supermolecular structure of the liposomes. Such stabilization can be detected, and in certain cases, caused by, the addition of magnesium or calcium ions.

46 Claims, No Drawings

LIPOSOME COMPOSITION FOR LUPUS ASSAY

The present application is a continuation-in-part application of application Ser. No. 410,249, filed Aug. 23, 1982, and a continuation-in-part application of application Ser. No. 362,382, filed Mar. 26, 1982, both of which are incorporated herein by reference.

TABLE OF CONTENTS

1. Field of the Invention
2. Background of the Invention
   2.1. Lupus
   2.2. Diagnostic Assays for Lupus
   2.3. Lipsomes
3. Brief Description of the Invention
   3.1. Lipsomes
   3.2. Diagnositic Assays
4. Advantages of the Invention
5. Detailed Description of the Preferred Embodiments
   5.1. Embodiment I
   5.2. Embodiment II
   5.3. Embodiment III
6. Examples
   6.1. Example 1: Preparation of Liposomes
   6.2. Example 2: Preparation for Anionic Lipids for Embodiment II
   6.3. Example 3: Embodiment I
   6.4. Example 4: Emodiment II
   6.5. Example 5: Embodiment III
   6.6. Example 6: Blind Studies

1. FIELD OF THE INVENTION

The present invention pertains to a systemic lupus erythematosis (SLE) antibody assay method utilizing novel liposome compositions. In particular, it involves a method for selectively detecting the presence of such antibodies which are produced by patients suffering from systemic lupus erythematosis. Thus, this assay can be used as a diagnostic tool in the detection of SLE.

2. BACKGROUND OF THE INVENTION

2.1. Lupus

SLE is a serious autoimmune condition in which abnormal humoral and cellular immune responses occur. This immune complex disorder manifests symptoms such as erosive inflammation of skin (producing a characteristic rash), blood vessel lesions, pleurisy, psychiatric disturbances, convulsions, and inflammation of the kidney glomeruli (leading to renal disfunction or failure). Although various factors have been attributed to the onset of SLE, the precise etiology is not known. It is known that significant concentrations of both gamma-globulin and complement are present in the tissues and such immune complexes are considered the causative agents for the systemic cellular damage which is observed. A wide range of auto-antibodies have been detected in SLE patients including circulating antibodies to lymphocytes, red blood cells, platelets and neutrophils and recognition occurs by all four subclasses of immunoglobulin to cellular components such as nuclei, ribosomes, mitochondria and lysosomes.

The sites of lupus antibody interaction with subcellular components include nucleoproteins, histones and nucleic acids. In the case of nucleic acids, one antigenic determinent appears to be the carbohydrate-phosphate unit.

2.2. Diagnostic Assays for Lupus

One of the first diagnostic tests for SLE involved the observation that microscopic examination of an SLE blood sample which is allowed to stand at room temperature for several hours reveals unusual structural entities which apparently result from leukocytic phagocytosis of extruded nuclei from damaged lymphocytes through which antinuclear antibodies had passed. Such polymorphonuclear leukocytes which possess multiple nuclei containing DNA-antiDNA complexes or such nuclei surrounded by multiple leukocytes, termed "LE cells", appear in 75% of patients with SLE. They also may appear however in patients which rheumatoid arthritis, Sjorgren's Syndrome, scleroderma and hepatitis B. The presence of LE cells as an SLE assay thus is non-specific, which coupled with a lack of specificity for immune complexes, makes results ambiguous and their interpretation subjective.

A further SLE screening test involves the agglutination reaction between circulating antibodies and polystyrene particles modified on their surface with dinitrophenyl groups. The interaction of these groups with Fab sites on immunoglobulins produces agglutination and precipitation of the particles. This test is essentially qualitative and lacks specificity for SLE antibodies alone, the modified particles interacting with any other circulating immunoglobulin so as to produce false positive results.

At present the most commonly used tests for SLE are immunofluorescent assays for the presence of cellular antinuclear antibodies. Human epithelial cells in vitro are exposed to serum of SLE patients and antibodies to cellular components which bind to these cells then are recognized by incubation with fluorescein isothicyanate linked anti-Ig. Various patterns of fluorescence can be correlated to antibodies for specific cell constituents; e.g., peripheral=anti-DNA, diffuse=anti-nucleoprotein, speckled=antiribonucleoprotein, nucleolar-=anti-RNA. This test is highly subjective and, as with the other tests discussed above, is not specific for SLE. Positive findings can be produced in patients with rheumatoid arthritis, scheroderma, Sjogren's Syndrome, liver disease, and pulmonary disease, as well as in patients receiving procainamide or hydralazine.

In another fluorescent assay, Clathridia protozoan are exposed to serum and the degree of binding to double stranded DNA in the connecticore is then recognized by incubation with fluorescein linked antibodies. This assay, while an improvement over the earlier methods, requires the use of a fluorescence microscope and detects only approximately 60% of those patients with lupus.

2.3. Liposomes

Liposomes are completely closed bilayer membranes containing an entrapped aqueous phase. Liposomes may be any variety of unilamellar vesicles (possessing a single membrane bilayer) or multilamellar vesicles (onion-like structures characterized by concentric membrane bilayers each separated from the next by a layer of water).

The original liposome preparations of Bangham et al. (1965, J. Mol. Biol. 13:238–252) involved suspending phospholipids in an organic solvent which was then evaporated to dryness leaving a waxy deposit of phospholipid on the reaction vessel. Then an appropriate amount of aqueous phase was added, the mixture was allowed to "swell", and the resulting liposomes which consisted of multilamellar vesicles (MLVs) were dispersed by mechanical means. The resulting structure of the membrane bilayer is such that the hydrophobic (non-polar) "tails" of the lipid orient inward while the hydrophilic (polar) "heads" orient outward towards the aqueous phase.

Lipid vesicles can also be prepared by injection of the lipids in an organic phase into an aqueous solution as described by Batzri and Korn (Biochim. Biophys. Acta, 298:1015 [1973]) using ethanol and by Deamer and Bangham (Biochim. Biophys. Acta, 443:629-634 [1976]) using ether.

3. BRIEF DESCRIPTION OF THE INVENTION

The present invention involves liposomes and diagnostic assays using them; the assays are based on the selective destabilization of liposomes and the inhibition thereof by SLE antibodies. For purposes of convenience the description of the invention will be divided into two major areas: the liposomes and the diagnostic assays.

3.1. Liposomes

Liposomes of the invention can be formed from certain amphipathic lipids. In contrast to lipid aggregates such as micelles and surface monolayers, liposomes involve self-sealing bilayers which form closed vesicles. Such bilayers can be produced from a number of flexible double tailed phosphatidylcholines of the formula

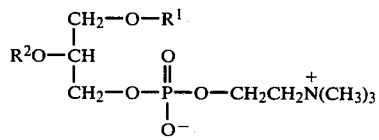

in which each of $R^1$ and $R^2$ is the acyl residue of the same or different fatty acid. $R^1$ and $R^2$ will generally have from 14 to 20 carbon atoms and may be saturated or unsaturated, e.g., tetradecanoyl, tetradec-9-enoyl, hexadecanoyl, hexadec-9-anoyl, octadecanoyl and octadec-9-enoyl. As noted, the $R^1$ and $R^2$ can be and often are different. Moreover, when unsaturation is present, the chain generally, but not necessarily, will define the cis configuration and will be present in the $R^2$ group. Most desirable $R^1$ and $R^2$ groups will be chosen to provide one double bond per phospholipid molecule. Particularly preferred are $R^1$ being palmitoyl (hexadecanoyl) and $R^2$ being oleoyl (cis-octadec-9-enoyl).

In addition to the double tailed phosphatidylcholine, there will be present a lipid which also serves as an antigen for antibodies specifically found in patients with SLE. Several such lipids are known but from the standpoint of availability, economics and performance, a phosphatidic acid or a cardiolipin (diphosphatidylglycerol) are preferred. The molar ratio of phosphatidylcholine to such lipid antigen will be from about 1:7 to about 7:1. One particularly satisfactory ratio is about 3:4 of phosphatidylcholine:lipid antigen.

It will be appreciated that multicomponent liposomes such as here described involve a high degree of component interaction and interdependency. Hence the interaction through van der Waal's attractive forces and steric repulsive forces of the various hydrophobic "tail" groups ($R^1$ and $R^2$) generally determine the nature of the bilayer's interior whereas steric effects, dipolar forces and electrostatic forces involving the hydrophilic "head" groups generally determine the nature of the bilayer's interfacial region. The nature of either group can also affect the nature of the other. The dynamic packing properties of the lipids which comprise a multicomponent liposome are determined by the complex interrelation of the component molecules.

It is desirable in some instances to incorporate a small amount of a rigid molecule such as a steroid (cholesterol or hydrocortisone) to modify the stability of the liposome. The presence of such rigid molecules in the liposome appears to alter the order of the hydrophobic tails of the phospholipid. Generally, this amount of steroid will be from about 5 to about 30 molar percent, based on the total amount of phosphatidylcholine and lipid antigen which is present. The influence of such stability altering components on the liposome involves a number of physicochemical characteristics which are easily determined but which are not characteristic of any given class of chemical compounds. Hence while cholesterol and dihydrocortisone will increase stability and reduce permeability of some liposome bilayers, they will decrease stability and increase permeability in others. Various thermodynamic and geometric theories explaining different properties of bilayer components have been proposed [see e.g., Israelachvili et al., Quat. Rev. Biophysics, 23 (2):121-200 (1980)], but in any event, the stabilizing effect of any given substance can be determined readily on an empirical basis utilizing spectrophotometric methods [see Weissmann et al., Proc. Nat. Acad. Sci. USA, 73, (2):510 (1976)].

In addition to the above components, the inclusion of a small amount, from about 10 to about 20 molar percent of the total amount of phosphatidylcholine and lipid antigen, of a liposome compatible negatively charged compound, e.g., a difatty acid phosphatidylglycerol or difatty acid alcohol phosphate ester, will be desirable. The function of this component, as for example dipalmitoylphosphatidylglycerol (DPPG) or dicetylphospate, is to increase the net negative surface charge of the bilayer. The addition of DPPG also confers stability. It has also been found desirable to include a small amount, e.g., from 1 to 5 molar percent based on the total amount of phosphatidylcholine and lipid antigen, of an antioxidant which is lipid-compatible, e.g., alpha-tocopherol.

It is preferred to use potassium or cesium salt forms of the anionic lipids, i.e., cardiolipin and dipalmitoylphosphatidylglycerol, since these forms substantially reduce false positive reactions in the final assay and increase solubility in solvent during the formation step. For example, liposomes formulated from the sodium, ammonium or lithium salts of anionic lipids while producing sporadic results for SLE, in some instances also produce false positives in the presence of rheumatoid factor. Thus, the sodium, ammonium and lithium salt forms should be avoided. The salt form is prepared by reacting a hydroxide of the metal selected with the free acid form of an anionic lipid. The free acid form of the anionic lipid is prepared by mixing a lipid with a solvent such as chloroform and adding polyanionic ion exchange beads. The suspension is then centrifuged and the supernatant containing the free acid of the lipid is removed. The free acid of the lipid is neutralized to pH 7 by the addition of the metal hydroxide to form the salt. Most preferably the cardiolipin is associated with cesium cation and dipalmitoylphosphatidylglycerol with the potassium cation.

A preferred bilayer composition includes phosphatidylcholine, cardiolipin, cholesterol, alpha-tocopherol and a phosphatidylglycerol in a molar ratio of about 3:4:1.9:0.1:1.

The liposome bilayers, prepared as hereafter defined, also have entrapped therein a metallochromic (colorimetric) indicator which is sensitive to divalent cations. For example, arsenazo III [2,7-bis-(2-arsenophenylazo)-1,8-dihydroxynaphthalene-3, 6-disulfonic acid] is normally red but turns blue in the presence of divalent metal cations, such as magnesium.

The liposomes of the present invention can be prepared by a modification of a number of known methods [which are reviewed by Szoka and Papahadjopoulos (Ann. Rev. Biosyps. Bioeng. 9:467-508 [1980]).

The preferred method involves injecting an ethereal solution of the bilayer components into a large volume of aqueous buffer solution containing the dye. Alternatively, lipids are prepared and dried, as by rotary evaporation from a suitable nonaqueous liquid such as chloroform, and combined with a solution of the indicator in buffer solution [0.145M NaCl-KCl, about 5 mM 4-2(2-hydroxyethyl)piperazine-2-ethane-sulfonic acid] to effect swelling and concommitant entrapment.

In either case the liposome mixture is chromatographed to separate excess, nonentrapped indicator from liposome-entrapped indicator, elution being readily monitored visually or by spectroscopy. Often it is advantageous or sometimes necessary to hold the liposome mixture under vacuum for a period of time, as for example, one or two hours, prior to chromatography in order to remove substantially all of the remaining solvent.

3.2. Diagnostic Assays

This invention involves three major embodiments (I, II, and III) for lupus diagnostic assays as described below. The present invention is based on the discovery that the increase in the permeability of the liposome bilayer which is observed in certain environments will be impeded or blocked by SLE antibodies. The antibodies are said to stabilize the liposome. "Stabilization" as used in the present invention refers to the preservation of the supramolecular structure or membrane architecture of the liposome. The precise mechanism by which this stabilization occurs is not fully understood. It is known that certain liposomes increase their permeability in the presence of divalent cations such as magnesium. Other liposomes are destabilized simply in the presence of normal serum. This destabilization will result in lysis of the liposome bilayer with release or "leakage" of any material which is entrapped therein. In some cases "leakage" refers to the movement (influx) of ions from the external environment into the aqueous spaces of the liposome. Surprisingly, however, this destabilization can be selectively blocked, i.e., the liposome structure is stabilized, by SLE antibodies. Consequently, by entrapping a metallochromic indicator within the liposome bilayer, the presence of SLE antibodies can be detected by observing the degree of blockage of the destabilization which is reflected by absence of a color change in the indicator.

4. ADVANTAGES OF THE INVENTION

The invention described herein has a number of advantages.

Firstly, by incorporation of the appropriate antigen into the liposomes, the binding of antibodies to the liposomes is restricted to those specific for diagnosis of SLE. Antibodies not specific for SLE will not bind.

Secondly, detection of antibodies is rapid and measured by simple colorimetric methods without the need for specialized equipment such as a fluorescence microscope.

Thirdly, both qualitative (visual) and quantitative (measured) aspects are possible in a single test, thereby allowing evaluation of antibody variation in a heterogeneous population of patients.

Fourthly, the test is exceedingly rapid; e.g., a response will be observed in a matter of minutes.

Lastly, the reagents used in the assay are non-toxic, non-radioactive, present no danger to the investigator, and do not require special handling.

5. DETAILED DESCRIPTION OF THE PREFERRED EMBODIMENTS

5.1. Embodiment I

In a first embodiment (I) of the present invention, a liposome composition is prepared which is susceptible to serum (normal) - induced leakage. For this purpose, it is preferable to utilize a phosphatidic acid as the lipid antigen in the liposomes, e.g., a liposome comprising a flexible double tailed phosphatidylcholine and a phosphatidic acid in a molar ratio of from about 1:7 to about 7:1, respectively, preferably from about 2:5 to about 4:3. A particularly desirable liposome comprises 3 molar parts of a phosphatidylcholine and 4 molar parts of phosphatidic acid (optionally together with the other components described above) with the indicator entrapped therein (as hereinafter described). Futhermore, 1-palimitoyl-2-oleoyl-phosphatidic acid is the preferred lipid antigen. Such liposomes will be stable in buffer but will demonstrate leakage in normal serum, thereby releasing the indicator. However, if such liposomes are first brought into contact with SLE serum, the leakage which would otherwise be observed is diminished or precluded. Consequently, challenge with a divalent metal cation to which the indicator is responsive, most notably magnesium, will produce a color change in the case of normal serum (and in fact serum from numerous diseased conditions) due to serum-induced leakage of the indicator. No color change (or one which develops at a far slower rate) will be observed in the case of a liposome which first is brought in contact with SLE serum.

5.2. Embodiment II

In a second embodiment (II) of the invention, a liposome composition is prepared similar to that described in Embodiment I but utilizing, cardiolipin in place of the phosphatidic acid. Such a composition will not develop leakage in the presence of serum (or for that matter in the presence of buffer). Leakage however can be induced by the addition of divalent ions such as magnesium. Again, such leakage is inhibited or reduced if the liposome is first brought in contact with SLE antibodies.

In this embodiment, therefore, the addition of magnesium ions not only induces leakage in the liposome composition, it also causes a color change in indicator which has "leaked" out of the liposome. In contrast, the same liposome composition which has come in contact with SLE serum will show no leakage (or leakage at a greatly reduced rate) in the presence of magnesium ions. Consequently little or no color change will occur.

The concentration of magnesium ion needed according to this embodiment is relatively small; generally a 5 to 80 millimolar solution is adequate. Excessively high concentrations should be avoided as these can produce leakage even in SLE serum treated liposomes. There also is an interplay between the liposome concentration and the amount of magnesium ion added and thus it is convenient to define a minimum lysis concentration (MLC) for each liposome composition; i.e., that concentration of magnesium ion which is just sufficient to effect release of the indicator from the liposome bilayer in the present of normal serum. This concentration can be easily determined by titration with increasing concentrations of magnesium ion.

5.3. Embodiment III

In a third embodiment (III) of the invention, liposomes containing a phosphatidic acid and a colorimetric indicator are used. When these liposomes are treated with $Ca^{++}$, a phase separation or clustering of the phosphatidic acid occurs resulting in the transport of $Ca^{++}$ to the interior of the liposome where it produces a color change in the indicator. When the antigen containing liposome is brought in contact with SLE antibodies, however, the antibodies bind to the antigen, inhibiting this clustering and thus stabilizing the membrane architecture of the liposome. $Ca^{++}$ will be transferred into the interior of the liposome at a very slow rate and no color change will be detected. (However, over time, there will be a gradual change in color.) Thus, as with the other embodiments, addition of SLE serum to the liposome, results in a little or no color change in the indicator.

The preferred liposome composition for this embodiment comprises a flexible double tailed phosphatidylcholine and a phosphatidic acid in molar ratios of from about 9:1 to about 3:7, respectively. The preferable phosphatidic acid is dipalmitoylphosphatidic acid and the preferable liposomes comprise egg phosphatidylcholine, dipalmitoylphosphatidic acid, cholesterol and dicetylphosphate in molar ratios of about 7:1:1:1, respectively.

While there are no critical operating conditions for the assay, they should be non-inhibiting and non-destructive. Aqueous media (other than magnesium solution) should be free of divalent metals such as calcium ion and preferably prepared from deionized water. Detergents and other chaotropic materials should be absent as should any impurities with which the antibodies may react.

6. Examples

The following examples will serve to further typify the nature of the invention without being a limitation on the scope thereof.

6.1. Example 1: Preparation of Liposomes

Liposomes are prepared according to a modification of the method of Deamer and Bangham (Biochim. Biophys. Acta, 443: 629–634 [1976]). All materials and equipment should be free of divalent metal cations. 1-Palimitoyl-2-oleoyl-phosphatidylcholine, cardiolipin, cholesterol, alpha-tocopherol and dipalmitoylphosphatidylglycerol in a 3:4:1.9:0.1:1 molar ratio are solubilized in petroleum ether. Ten milliliters of ether solution (40 micromoles of lipid) are placed in a 20 ml glass syringe with a Teflon plunger which is attached to a vertical infusion pump.

A suspension of 4.5 mM arsenazo III (hereinafter A III) in 2 ml of 5 mM Hepes buffer (N-2-hydroxyethylpiperazine-N'-2-ethanesulfonic acid) at pH 7.2, containing 0.145M NaCl/KCl is placed in Leibig condenser into which a rubber stopper (bottom opening) has previously been placed. The condenser is heated to 54° C. with a circulating water bath and nitrogen is bubbled through the aqueous phase. A 22 guage needle is inserted through the rubber stopper at the bottom of the condenser.

The petroleum ether phase is then injected into the aqueous phase at a rate of 0.5 ml/min. As the ether evaporates and escapes, the liposome suspension remains. This suspension is passed through a column of Sepharose 4B, eluting with buffer, to remove excess and unsequestered A III, the liposome-entrapped A III (red) being eluted from the column in the void volume. Optionally the suspension to be chromatographed can be held under vacuum (water aspirator) for from about one to five hours to remove excess petroleum ether prior to passage through the column. This material is then diluted with Hepes buffer to a concentration at which one can best distinguish between lupus positive sera and normal sera. This is typically an optical density of approximately 0.12 at 750 nanometers.

6.2. Example 2: Preparation of Anionic Lipids for Embodiment II

Three grams of 100–200 mesh beads of sulfonated polystyrene (Biorad AG50W-X8) are washed once with 1:1 methanol:water and three times with 1:1 methanol:chloroform. Twenty-five mg of cardiolipin (commercially obtained, sodium salt) are added and allowed to remain in contact with the beads for 2 minutes. The cardiolipin (free acid) is separated from the suspension by centrifugation and titrated with 0.1M cesium hydroxide in methanol to pH 7. Recovery is determined by a Bartlett assay for inorganic phosphate (Kates, "Technology of Lipidology", North-Holland American Elsevier, 1975). The product should produce a single spot on TLC (65:25:4 chloroform:methanol:water).

Following the same procedure with dipalmitoylphosphatidylglycerol (sodium salt) but titrating with 0.1M methanolic potassium hydroxide, there is obtained the potassium salt form.

These materials, namely cardiolipin (cesium salt) and dipalmitoylphosphatidylglycerol when utilized in the procedure of Example 1 produce a liposome composition of increased selectivity to SLE antibodies.

6 3. Example 3: Embodiment I

As an example of Embodiment I, liposomes are prepared according to the procedure of Example 1 utilizing, however, phosphatidic acid in place of cardiolipin. When utilized in the actual assay, leakage will occur upon addition of the serum. The leakage will be detected upon addition of magnesium ion.

6.4. Example 4: Embodiment II

As an example of Embodiment II, aliquots of the liposomes (red) are placed in two glass tubes. To one tube is added an SLE test serum and to the other normal serum (control). Based upon the volume in each tube, a serum dilution equal to 1:16 may be prepared. (In practice, several different dilutions, and therefore several tubes, could be used). The same dilution is made for both the SLE test serum and normal serum. After serum addition, the liposomes are incubated for 1 to 5 minutes at about 25° C. Following the incubation, magnesium chloride solution (e.g., 50 mM final concentration) is added to each of the tubes. The normal serum control will turn blue within 5 minutes while the lupus serum test sample will remain red for at least 3 hours longer than the normal serum.

Alternatively, the test sample and normal serum control are serially diluted. If at any dilution there is a substantial delay in the color change induced by the test sample as compared to the serum control, the test is considered positive.

6.5. Example 5: Embodiment III

As an example of Embodiment III, one hundred microliters of liposomes (red) are placed in three glass tubes and diluted with Hepes buffer up to 0.2 ml. One tube constitutes a buffer blank, the second is an SLE test serum and the third serves as a normal serum control. Based upon the 0.3 ml volume in each tube, a serum dilution equal to 1:16 is calculated. (In practice, several different dilutions, and therefore several tubes, could be used). The same dilution is made for both the SLE test serum and normal serum. After serum addition, the liposomes are incubated for 5 minutes at about 25° C. Following the incubation, 80 mM calcium chloride (final concentration) is added to each of the tubes. The buffer control will turn blue within 10 minutes. The normal serum control will turn blue before 30 minutes, and the lupus serum test will remain red for at least 30 minutes longer than the normal serum. Alternatively, the test sample and normal serum control are serially diluted. If at any dilution there is a substantial delay in the color change induced by the test sample as compared to the serum control, the test is considered positive.

6.6. Example 6: Blind Studies

A blind study (involving Embodiment II) included serum samples from the following sources: known lupus patients, patients exhibiting clinical symptoms of lupus but a negative clathridia test, patients showing antinuclear antibodies but no clinical symptoms, patients with scleroderma, patients with a positive VDR test (syphilis), patients with Sjogren's Syndrome and normal patients. The assay gave a proper response in 19 out of 20 unknowns. The only false negative was a patient suffering from both syphilis and lupus. Significantly, and in contrast to other tests, a patient with syphilis but not lupus did not produce a false positive.

In a second blind study of 80 samples of sera (also involving Embodiment II) which included previously diagnosed rheumatoid arthritis, scleroderma, Sjogren's Syndrome, mixed connective tissue disease, and controls, the following results were obtained:

|  | No. Tested | Positive | Negative |
| --- | --- | --- | --- |
| SLE | 19 | 17 | 2 |
| Rheumatoid Arthritis | 19 | 4 | 15 |
| Scleroderma | 14 | 0 | 14 |
| Sjogren's Syndrome | 2 | 0 | 2 |
| MCTD | 2 | 2 | 0 |
| Controls | 24 | 1 | 23 |

While the invention has been described with reference to its preferred embodiments thereof, it will be appreciated by those of ordinary skill in the art that various changes can be made in the process and compositins without departing from the basic spirit and scope of the invention.

What is claimed is:

1. A method for detecting SLE antibodies in serum, comprising:
   (a) contacting serum, for a period of time at least sufficient to permit equilibration of binding between SLE antibodies and cardiolipin, with liposomes having a multicomponent liposome bilayer comprising a flexible double tailed phosphatidylcholine and cardiolipin in a molar ratio of from about 1:7 to about 7:1, respectively;
   (b) exposing said liposomes to conditions which cause destablization of the liposomes in the absence of SLE antibodies and which do not cause destablization of the liposomes in the presence SLE antibodies; and
   (c) detecting any destablization of the liposomes, said method being performed under conditions non-inhibiting to the binding between SLE antibodies and said cardiolipin.

2. The method according to claim 1, wherein said ratio is from about 2:5 to about 4:3.

3. The method according to claim 1, wherein said liposomes contain entrapped therein a divalent cation responsive colorimetric indicator, and said conditions causing destablization comprise contacting said liposomes with divalent cations which results in leakage and a change in color of the indicator.

4. The method according to claim 3, wherein the divalent cations are magnesium or calcium cations.

5. A method for detecting SLE antibodies in serum, comprising:
   (a) contacting serum, for a period time sufficient to permit equilibration of binding between SLE antibodies and a phosphatidic acid antigen which binds to SLE antibodies, with liposomes having a multicomponent liposome bilayer comprising a flexible double tailed phosphatidylcholine and said phosphatidic acid antigen in molar ratios of from about 9:1 to about 3:7, respectively, said liposomes being unstable in the presence of calcium ions unless SLE antibodies are present;
   (b) exposing said liposomes to calcium ions; and
   (c) detecting any destabilization of the liposomes, said method being performed under conditions non-inhibiting to the binding between SLE antibodies and said phosphatidic acid antigen.

6. The method according to claim 5, wherein said phosphatidic acid is dipalmitoylphosphatidic acid, and said liposomes have a multicomponent liposome bilayer comprising egg phosphatidylcholine, dipalmitoylphosphatidic acid, cholesterol and dicetylphosphate in molar ratios of about 7:1:1:1, respectively.

7. The method according to claim 5, wherein said liposomes contain entrapped therein a divalent cation responsive colorimetric indicator, and said destablization results in an influx of divalent cations into the liposomes which results in a change in color of the indicator.

8. A method for detecting SLE antibodies in serum, comprising:
   (a) contacting serum, for a period of time at least sufficient to permit equilibration of binding between SLE antibodies and a phosphatidic acid antigen which binds to SLE antibodies, with liposomes having a multicomponent liposome bilayer comprising a flexible double tailed phosphatidylcholine and said phosphatidic acid antigen in a molar ratio of from about 1:7 to about 7:1, respectively, said liposomes being stable in the presence of serum containing SLE antibodies and unstable in the presence of serum not containing SLE antibodies; and (b) detecting any liposome instability, said method being performed under conditions non-inhibiting to the binding between SLE antibodies and said phosphatidic acid antigen.

9. The method according to claim 8, wherein said ratio is from about 2:5 to about 4:3.

10. The method according to claim 8, wherein said phosphatidic acid is 1-palmitoyl-2-oleoylphosphatidic acid.

11. The method according to claim 8, wherein said liposomes contain entrapped therein a colorimetric indicator, and said instability is detected by a color change in said indicator which is released from the liposomes in the absence of SLE antibodies.

12. The method according to claim 11, wherein said indicator is responsive to divalent metal ions and is exposed to divalent cations upon release from the liposomes.

13. The method according to claim 12, wherein the divalent metal ions are magnesium ions.

14. The method according to claim 1, 5 or 8, wherein the anionic lipid components of the bilayer are cesium or potassium salts.

15. The method according to claim 1, 5 or 8, wherein said phosphatidylcholine is 1-palmitoyl-2-oleoylphosphatidylcholine.

16. The method according to claim 1, 5 or 8, wherein said liposome bilayer contains a stabilizing amount of a rigid steriod stabilizer.

17. The method according to claim 16, wherein said steroid is cholesterol.

18. The method according to claim 17, wherein the stabilizing amount is from about 5 to about 30 molar percent, relative to the total amount of said phosphatidylcholine and phosphatidic acid or cardiolipin.

19. The method according to claim 1 or 8, wherein said liposome bilayer contains from about 10 to about 20 molar percent, relative to the total amount of said phosphatidylcholine and phosphatidic acid or cardiolipin, of a liposome compatible negatively charged compound.

20. The method according to claim 19, wherein said liposome compatible negatively charged compound is phosphatidylglycerol.

21. The method according to claim 20, wherein said phosphatidylglycerol is dipalmitoyl-phosphatidyl glycerol.

22. The method according to claim 5, wherein said liposome bilayer contains from about 10 to about 20 molar percent, relative to the total amount of phosphatidylcholine and phosphatidic acid, of dicetylphosphate.

23. The method according to claim 1, 5 or 8, wherein said liposome bilayer contains a stabilizing amount of an antioxidant.

24. The method according to claim 23, wherein said antioxidant is alpha-tocopherol in an amount corresponding to from about 1 to about 5 molar percent of the total amount of said phosphatidylcholine and phosphatidic acid or cardiolipin.

25. The method according to claim 1, wherein said bilayer comprises 1-palmitoyl-2-oleoylphosphatidylcholine, cardiolipin, cholesterol, alpha-tocopherol and dipalmitoyl phosphatidylglycerol in a molar ratio of about 3:4:1.9:0.1:1, respectively.

26. The method according to claim 8, wherein said bilayer comprises 1-palmitoyl-2-oleoylphosphatidylcholine, 1-palmitoyl-2-oleoyl-phosphatidic acid, cholesterol, alpha-tocopherol and dipalmitoyl phosphatidylglycerol in a molar ratio of about 3:4:1.9:0.1:1, respectively.

27. The method according to claim 1, 5 or 8, wherein said indicator is arsenazo III.

28. A liposome composition comprising liposome vesicles, said vesicles having (i) a multicomponent liposome bilayer comprising a flexible double tailed phosphatidylcholine and a lipid antigen for SLE antibodies in a molar ratio of from about 1:7 to about 9:1, respectively, and (ii) a colorimetric indicator entrapped within said liposome.

29. A composition according to claim 28, wherein said indicator is a divalent cation responsive colorimetric indicator.

30. A composition according to claim 28, wherein said ratio is from about 2:5 to about 4:3.

31. A composition according to claim 28, wherein said lipid antigen is a phosphatidic acid or cardiolipin.

32. A composition according to claim 28, wherein said phosphatidylcholine is 1-palimitoyl-2-oleoylphosphatidylcholine.

33. A composition of claim 28, wherein said vesicles have a multicomponent liposome bilayer comprising egg phosphatidylcholine, dipalmitoylphosphatidic acid, cholesterol and dicetylphosphate in molar ratios of about 7:1:1:1, respectively.

34. A composition according to claim 28, wherein said liposome bilayer contains a stabilizing amount of a rigid steroid stabilizer.

35. A composition according to claim 34, wherein said steriod is cholesterol.

36. A composition according to claim 34, wherein the stabilizing amount is from about 5 to about 30 molar percent, relative to the total of amount of said phosphatidylcholine and said lipid antigen.

37. A composition according to claim 28, wherein said liposome bilayer contains from about 10 to about 20 molar percent, relative to the total of said phosphatidylcholine and said lipid antigen, of a liposome compatible negatively charged compound.

38. A composition according to claim 37, wherein said liposome compatible negatively charged compound is a phosphatidylglycerol.

39. A composition according to claim 38, wherein said phosphatidylglycerol is dipalmitoyphosphatidylgylycerol.

40. A composition according to claim 28, wherein said liposome bilayer contains a stabilizing amount of an antioxidant.

41. A composition according to claim 40, wherein said antioxidant is alpha-tocopherol in an amount corresponding to from about 1 to about 5 molar percent of the total amount of said phosphatidylcholine and said lipid antigen.

42. A composition according to claim 28, wherein said liposome bilayer comprises 1-palmitoyl-2-oleoyl-phosphatidylcholine, cardiolipin, cholesterol, alpha-tocopherol and dipalmitoyl phosphatidylglycerol in a molar ratio of about 3:4:1.9:0.1:1, respectively.

43. A composition according to claim 28, wherein said liposome bilayer comprises 1-palmitoyl-2-oleoylphosphatidylcholine, 1-palmitoyl-2-oleoyl-phosphatidic acid, cholesterol, alpha-tocopherol and dipalmitoylphosphatidylglycerol in a molar ratio of about 3:4:1.9:0.1:1, respectively.

44. A composition according to claim 28 or 42, wherein said indicator is arsenazo III.

45. A composition according to claim 28, wherein said lipid antigen is a cesium or potassium salt.

46. A composition according to claim 28, wherein said lipid antigen is the cesium salt of cardiolipin and wherein said liposome bilayer further comprises the potassium salt of dipalmitoylphosphatidylgycerol.

* * * * *

UNITED STATES PATENT AND TRADEMARK OFFICE
CERTIFICATE OF CORRECTION

PATENT NO.    : 4,564,599

DATED         : January 14, 1986

INVENTOR(S)   : Andrew S. Janoff, Marc J. Ostro; Alan L. Weiner, Gerald Weissmann; James R. Seibold It is certified that error appears in the above-identified patent and that said Letters Patent is hereby corrected as shown below:   Title page On page 1, correct one of co-inventors, by deleting "Allan L. Weiner" and inserting --Alan L. Weiner--.

On page 1, correct the name of the Assignee by deleting "The Lipodome Company, Inc." and inserting --The Liposome Company, Inc.--.

Signed and Sealed this

Twenty-seventh Day of May 1986

[SEAL]

Attest:

DONALD J. QUIGG

Attesting Officer

Commissioner of Patents and Trademarks